(12) United States Patent
Fisher et al.

(10) Patent No.: US 10,214,503 B2
(45) Date of Patent: Feb. 26, 2019

(54) 2-(2,3-EPDXYPROPYL)PHENOL COMPOSITION AND METHOD OF MAKING

(71) Applicant: SABIC Global Technologies, B.V., Bergen op Zoom (NL)

(72) Inventors: Scott Michael Fisher, Delmar, NY (US); Madhav Ghanta, Delmar, NY (US); Mark R. Denniston, Altamont, NY (US)

(73) Assignee: SABIC GLOBAL TECHNOLOGIES B.V., Bergen op Zoom (NL)

( * ) Notice: Subject to any disclaimer, the term of this patent is extended or adjusted under 35 U.S.C. 154(b) by 122 days.

(21) Appl. No.: 15/329,279

(22) PCT Filed: Aug. 25, 2015

(86) PCT No.: PCT/US2015/046633
§ 371 (c)(1),
(2) Date: Jan. 26, 2017

(87) PCT Pub. No.: WO2016/032997
PCT Pub. Date: Mar. 3, 2016

(65) Prior Publication Data
US 2017/0260152 A1    Sep. 14, 2017

Related U.S. Application Data

(60) Provisional application No. 62/042,312, filed on Aug. 27, 2014.

(51) Int. Cl.
C07D 301/12    (2006.01)
C08G 59/02    (2006.01)
(Continued)

(52) U.S. Cl.
CPC ........... *C07D 301/12* (2013.01); *C08G 59/02* (2013.01); *C07C 33/03* (2013.01); *C07C 33/20* (2013.01); *C07C 33/30* (2013.01); *C07D 311/20* (2013.01)

(58) Field of Classification Search
None
See application file for complete search history.

(56) References Cited

U.S. PATENT DOCUMENTS 3,281,393 A    10/1966 Tsou et al.
2005/0090673 A1    4/2005 Pews

FOREIGN PATENT DOCUMENTS

| GB | 1399639 | 7/1975 |
| JP | 04183707 | 6/1992 |
| JP | 2006342157 A | * 12/2006 |

OTHER PUBLICATIONS

Lattanzi et al., "VO(acac)2/TBHP Catalyzed Epoxidation of 2-(2-Alkenyl)phenols. Highly Regio- and Diastereoselective Oxidative Cyclization to 2,3-Dhydrobenzolfuranols and 3-Chromanols," Synlett, No. 6, pp. 942-946, 2002. (Year: 2002)*

(Continued)

*Primary Examiner* — Randy P Gulakowski
*Assistant Examiner* — Ha S Nguyen
(74) *Attorney, Agent, or Firm* — Cantor Colburn LLP

(57) ABSTRACT

Disclosed herein is a method of making a 2-(2,3-epoxypropyl)phenol by reacting a 2-allylphenol with an oxidant in the presence of a catalyst. A 3-chromanol can be formed as a by-product. The method can be used to make 2-(2,3-epoxypropyl)-6-methylphenol. Transition metal catalysts and peroxide oxidants can be used. Also disclosed is a composition comprising 1 to 90 weight percent of a 2-(2,3-epoxypropylphenol, 5 to 90 weight percent of a 2-allylphenol, and 0 to 40 weight percent of a 3-chromanol, and in particular, a composition comprising 1 to 90 weight percent 2-(2,3-

(Continued)

epoxypropyl)-6-methylphenol, 5 to 90 weight percent 2-allyl-6-methylphenol, and 0 to 40 weight percent 8-methyl-3-chromanol.

2 Claims, 6 Drawing Sheets

(51) Int. Cl.
  *C07D 311/20* (2006.01)
  *C07C 33/20* (2006.01)
  *C07C 33/03* (2006.01)
  *C07C 33/30* (2006.01)

(56) References Cited

OTHER PUBLICATIONS

Satyanarayana et al., "A New and Facile Synthesis of Chroman-3-ols, 3,4-Dihydro-2H[1]-Benzopyran-3-ols," Synthetic Communications, 21(14), pp. 1455-1464 (1991). (Year: 1991).*
Sheldon et al., "Metal-Catalyzed Epoxidation of Olefins with Organic Hydroperoxides: I. A Comparison of Various Metal Catalysts," Journal of Catalysts, 31, pp. 427-437 (1973). (Year: 1973).*
Battioni et al.; "Monooxygenase-like oxidation of hydrocarbons by H2O2 catalyzed by manganese porphyrins and imidazole: selection of the best catalytic system and nature of the active oxygen species"; J. Am. Chem. Soc., vol. 110; 1988; pp. 8462-8470.
Bottcher et al.; "Aerobic oxidation of hydrocarbons catalyzed by electronegative iron salen complexes"; J. of Mol. Catal. A: Chem., vol. 113; 1996; pp. 191-200.
Bruno et al; "Synthesis and catalytic properties in olefin epoxidation of dioxomolybdenum (VI) omplexes bearing a bidentate or tetradentate salen-type ligand"; J. of Mol. Cat. A: Chem., vol. 270; 2007; pp. 185-194.
Conte et al., "Liquid phase oxidation reactions by peroxides in presence of vanadium complexes", Appl. Catal. A: Gen., 1997, vol. 157; pp. 335-361.
Farias et al.; "Epoxidation of soybean oil using a homogeneous catalytic system based on a molybdenum (VI) complex"; Applied Catal. A: Gen., vol. 384; 2010; pp. 213-219.
Grivani et al; "Epoxidation of alkenes by a highly reusable and efficient polymer-supported molybdenum carbonyl catalyst"; Catal. Commun., vol. 6; 2005; pp. 375-378.
Groves et al.; "Epoxidation Reactions Catalyzed by Iron Porphyrins. Oxygen transfer from Iodosylbenzene"; J. Am. Chem. Soc., vol. 105; 1983; pp. 5786-5791.
Joseph et al; "Studies on vanadium catalyzed direct hydroxylation of aromatic hydrocarbons using hydrogen peroxide as oxidant"; Catal. Tod., vol. 141; 2009; pp. 211-214.
Krackl et al.; "Low-Valent Molybdenum-Based Dual Pre-Catalysts for Highly Efficient Catalytic Epoxidation of Alkenes and Deoxygenation of Sulfoxides" Chem. Cat. Chem.; 2011; pp. 1186-1192.
Kunai et al.; "The role of oxygen in the hydroxylation reaction of benzene with Fenton's reagent. 18O tracer study"; J. Am. Chem. Soc., vol. 108, No. 19; 1986; pp. 6012-6016.
Madeira et al.; "Epoxidation of cis-cyclooctene using diamine bis(phenolate) vanadium, molybdenum and tungsten complexes as catalysts"; Inorg. Chimi. Acta., vol. 383; 2012; pp. 152-156.
Mansuy et al.; "In the presence of imidazole, iron- and manganese-porphyrins catalyse the epoxidation of alkenes by alkyl hydroperoxides"; J. of Chem. Soc. Chem. Commun.; 1984; pp. 1255-1257.
Meunier et al.; "Sodium hypochlorite: A convenient oxygen source for olefin epoxidation catalyzed by (Poryphyrinato) manganese complexes"; J. Am. Chem. Soc., vol. 106; 1984; pp. 6668-6676.
Renaud et al.; "A very efficient system for alkene epoxidation by hydrogen peroxide: catalysis by Mn-porphyrin in presence of imidazole"; J. Chem. Soc. Chem. Commun.; 1985; pp. 888-889.
Salamao et al.; "Oxidation of cyclohexane promoted by Fe(III)salen Cl and Mn(III)salen Cl"; Catal. Commun., vol. 8; 2007; pp. 69-72.
Sharpless et al; "High stereo- and regioselectivities in the transition metal catalyzed epoxidations of olefinic alcohols by TBHP"; JACS, vol. 95, No. 18; 1973; pp. 6136-6137.
Skobelev et al.; "Efficient epoxidation of olefins by H2O2 catalyzed by iron "helmet" phthalocyanines"; ChemComm., vol. 49; 2013; pp. 5577-5579
Sobczak et al.; "Molybdenum complex-catalyzed epoxidation of unsaturated fatty acids by organic hydroperoxides"; Appl. Catal. A: Gen., vol. 248; 2003; pp. 261-268.
Sugimoto et al.; "Iron(II)-induced activation of hydroperoxides for the dehydrogenation and monooxygenation of organic substrates in acetonitrile"; J. Am. Chem. Soc., vol. 107; 1985; pp. 5712-5716
Traylor et al.; "Mechanisms of reactions of iron(III) porphyrins with hydrogen peroxide and hydroperoxides: solvent and effects"; J. Am. Chem. Soc., vol. 112; 1990; pp. 178-186.
Traylor et al.; "Sterically protected hemins with electronegative substituents: Efficient catalysts for hydroxylation and epoxidation"; J. Chem. Soc. Chem. Commun.; 1984; pp. 279-280.
Wei et al.; "CO2-expanded solvents: Unique and versatile media for performing homogenous catalytic oxidations"; JACS, vol. 124, No. 11; 2002; pp. 2513-2517.
Fukuhara et al.; "Synthesis of thermosetting poly)phenylene ether) containing allyl groups"; Polymer 45; (2004) pp. 843-847.
Hirooka et al.; "Efficient Synthesis of Optically Active Gallocatechin-3-gallate Derivatives via 6-endo-Cyclization"; SYNLETT (2008); No. 20; pp. 3234-3238.
Huang et al.; "Synthesis of New Thermosetting Poly)2,6-dimethyl-1, 4-phenylene oxide)s Containing Epoxide Pendant Groups"; J. of Polymer Sci: Part A: Polymer Chemistry, vol. 44; pp. 5875-5886; (2006).
International Search Report for International Application No. PCT/US2015-046633; International Filing Date Aug. 25, 2015; dated Apr. 29, 2016; 3 pages.
Kim et al.; "Enzymatic epoxidation and polymerization of cardanol obtained from a renewable resource and curing of epoxide-containing polycardanol"; J. of Molecular Catalysis B; Enzymatic 45; (2007); pp. 39-44.
Lattanzi et al.; "VO(acac)2/TBHP Catalyzed Epoxidation of 2-(2-Alkenyl)phenols. Highly Regio- and Diastereoselective Oxidative Cyclization to 2,3-Dihydrobenzofuranols and 3-Chromanols"; Synlett 2002; vol. 2002; No. 6; pp. 942-946.
Maheswari et al.; "A Na2WO4/H2WO4-Based Highly Efficient Biphasic Catalyst towards Alkene Epoxidation, using Dihydrogen Peroxide as Oxidant"; Adv. Synth. Catal.; 2005; vol. 347; pp. 1759-1764.
Nishide et al.; "Oxidative polymerization of 2-(2-Butenyl)- and 2-(3-Methyl-2-butenyl)-6-methylphenol"; Makromol. Chem. 183; (1982); pp. 1889-1895.
Pansevich et al.; "Investigations in the Field of Alcohol Oxides (Oxidols)"; J. of General Chemistry of the U.S.S.R.; vol. XXIV; No. 5; May 1954; 7 pages.
Sheldon et al.; "Metal-Catalyzed Epoxidation of Olefins with Organic Hydroperoxides"; J. of Catalysis 31; (1973); 12 pages.
Written Opinion of the International Search Report for International Application No. PCT/US2015-046633; International Filing Date Aug. 25, 2015; dated Apr. 29, 2016; 6 pages.

* cited by examiner

2-(2,3-EPDXYPROPYL)PHENOL COMPOSITION AND METHOD OF MAKING

CROSS REFERENCE TO RELATED APPLICATIONS

This application is a National Stage application of PCT/US2015/046633, filed Aug. 25, 2015, which claims the benefit of U.S. Provisional Application No. 62/042,312, filed Aug. 27, 2014, both of which are incorporated by reference in their entirety herein.

BACKGROUND OF THE INVENTION 2-(2,3-epoxypropyl)phenols are C-glycidylphenols in which the 2,3-epoxypropyl or glycidyl group is directly bonded to a phenyl ring carbon atom, and are differentiated from O-glycidylphenols, or glycidyl phenyl ethers, in which the glycidyl group is bonded to the phenol oxygen atom. 2-(2,3-epoxypropyl)phenols are potentially useful reactants in thermoset resins, and in particular, in epoxy resins, by virtue of their epoxy functionality. In order to become a material of commerce, an efficient, low cost method of manufacturing 2-(2,3-epoxypropyl)phenols is desirable. In order to be low cost, the method should have the following characteristics. It should be based on low-cost materials that are available in bulk quantities, it should be a one-step reaction, and it should have a commercially acceptable cycle time (time between batches in batch manufacturing).

BRIEF DESCRIPTION OF THE INVENTION

A method of making a 2-(2,3-epoxypropyl)phenol comprises reacting a 2-allylphenol with an oxidant in the presence of a catalyst wherein the 2-allylphenol comprises

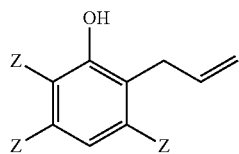

and the 2-(2,3-epoxypropyl)phenol comprises

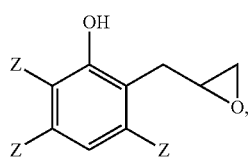

wherein each occurrence of Z is independently hydrogen, halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, or $C_2$-$C_{12}$ halohydrocarbyloxy wherein at least two carbon atoms separate the halogen and oxygen atoms; and wherein all weight percents are based on the total weight of the 2-(2,3-epoxypropyl)phenol, the 2-allylphenol, and the 3-chromanol.

In another embodiment, a method of making 2-(2,3-epoxypropyl)-6-methylphenol, comprises reacting 2-allyl-6-methylphenol with an oxidant comprising m-chloroperbenzoic acid in the presence of a catalyst comprising bis(acetylacetonate)dioxomolybdenum (VI), tungstic acid, tungsten hexacarbonyl, or combination thereof.

In another embodiment, a composition comprises, based on the total weight of the composition: 1 to 90 weight percent of a 2-(2,3-epoxypropyl)phenol of structure

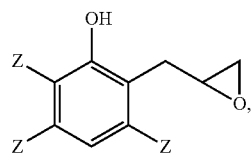

5 to 90 weight percent of a 2-allylphenol of structure

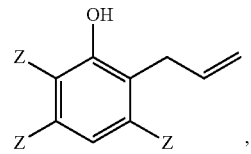

and 0 to 40 weight percent of a 3-chromanol of structure

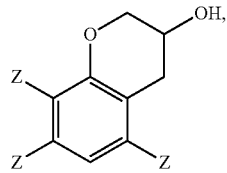

wherein each occurrence of Z is independently hydrogen, halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, or $C_2$-$C_{12}$ halohydrocarbyloxy wherein at least two carbon atoms separate the halogen and oxygen atoms; wherein all weight percents are based on the total weight of the 2-(2,3-epoxypropyl)phenol, the 2-allylphenol, and the 3-chromanol.

Another embodiment is a thermoset polymer made by reacting a 2-allylphenol of structure

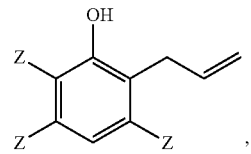

wherein each occurrence of Z is independently hydrogen, halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, or $C_2$-$C_{12}$ halohydrocarbyloxy wherein at least two carbon atoms separate the halogen and oxygen atoms, with an oxidant in the presence of a catalyst.

BRIEF DESCRIPTION OF THE DRAWINGS

Referring now to the drawings.

DETAILED DESCRIPTION OF THE INVENTION

Figure 1:
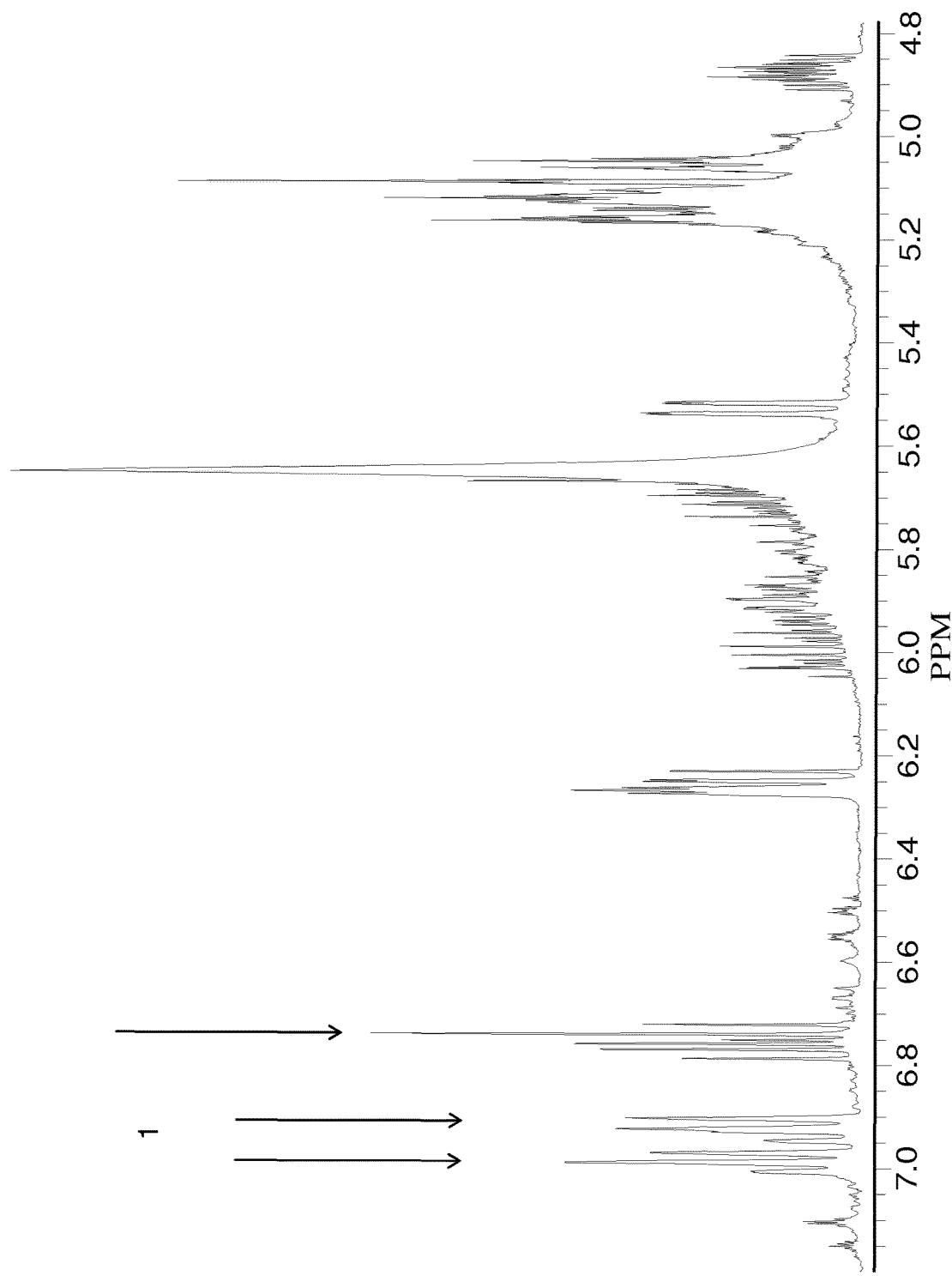
FIG. 1 depicts the 400 Mhz $^1$H-NMR spectrum of the reaction mixture from Ex. 4, which contains methanol, unreacted 2-allyl-6-methylphenol, 8-methyl-3-chromanol, and hydrogen peroxide.

In order to become materials of commerce, an efficient, low cost method of manufacturing 2-(2,3-epoxypropyl)phenols is desirable. The inventors have determined a direct, one-step route for the manufacture of 2-(2,3-epoxypropyl) phenols which is epoxidation of the corresponding 2-allylphenols. 2-allylphenols are allylphenols in which the allyl group is directly bonded to a phenyl carbon atom, and are differentiated from O-allylphenols, in which the allyl group is directly bonded to the phenolic oxygen. The method is applicable to 2-allylphenols, such as 2-allyl-6-methylphenol, and can utilize commercially available peroxides, for example m-chloroperbenzoic acid. The method has one reaction step—epoxidation of a 2-allylphenol. Moreover, conversion of the 2-allylphenol can proceed quickly, which provides commercially acceptable cycle times.

Thus, a method of making a 2-(2,3-epoxypropyl)phenol comprises reacting a 2-allylphenol with an oxidant in the presence of a catalyst; wherein the 2-allylphenol comprises:

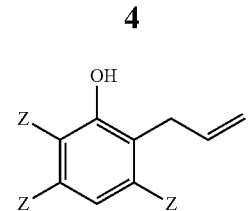

and the 2-(2,3-epoxypropyl)phenol comprises:

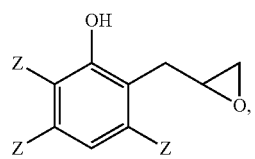

wherein each occurrence of Z is independently hydrogen, halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, or $C_2$-$C_{12}$ halohydrocarbyloxy wherein at least two carbon atoms separate the halogen and oxygen atoms; and wherein all weight percents are based on the total weight of the 2-(2,3-epoxypropyl)phenol, the 2-allylphenol, and the 3-chromanol. As used herein, the term "hydrocarbyl" refers broadly to a mono-valent substituent comprising carbon and hydrogen, optionally with 1 to 3 heteroatoms, for example, oxygen, nitrogen, halogen, silicon, sulfur, or combination thereof. In some embodiments, the Z groups are selected from hydrogen, methyl, and combination thereof. For example, the method can be used to make 2-(2,3-epoxypropyl)-6-methylphenol from 2-allyl-6-methylphenol.

The catalyst can be a transition metal catalyst. For example, the catalyst can be a transition metal catalyst comprising molybdenum, vanadium, tungsten, titanium, manganese, niobium, or combination thereof. The transition metal can be in the IV, V, or VI oxidation state, for example Ti(IV), Nb(V), Mn(VI), Mo(VI), or W(VI), Specific catalysts include, but are not limited to, bis(acetylacetonato) dioxomolybdenum(VI) ($MoO_2(acac)_2$), molybdenum dichloride dioxide ($MoO_2Cl_2$), tungstic acid ($H_2WO_4$), tungstosilicic acid ($H_4O_{40}SiW_{12}$·$xH_2O$), tungsten hexacarbonyl ($W(CO)_6$), molybdenum hexacarbonyl ($Mo(CO)_6$), vanadium acetylacetonate ($V(acac)_3$), vanadyl acetylacetonate ($VO(acac)_2$), vanadium pentoxide ($V_2O_5$), or combination thereof. In some embodiments, the catalyst comprises bis(acetylacetonato)dioxomolybdenum(VI), molybdenum dichloride dioxide, tungstic acid, tungsten hexacarbonyl, or combination thereof. The catalyst can also be a heterogeneous catalyst on an inert solid support, for example silica or alumina.

The oxidant can comprise an organic peroxide, i.e. an organic compound containing a peroxy "—O—O—" group. In particular, the oxidant can comprise hydrogen peroxide, an alkyl peroxide, an alkyl hydroperoxide, a ketone peroxide, a diacyl peroxide, a diperoxy ketal, a peroxyester, a peroxydicarbonate, a peroxy acid, a perbenzoic acid, or combination thereof. Examples of oxidants include hydrogen peroxide, 2-butanone peroxide, cyclohexanone peroxide, benzoyl peroxide, lauryl peroxide, di-tert-butyl peroxide, tert-butyl cumyl peroxide, dicumyl peroxide, tert-butyl hydroperoxide, cumene hydroperoxide, tert-butyl peroxybenzoate, tert-amyl peroxbenzoate, tert-butyl peroxyoctoate, 2,2-di(tert-butylperoxy)butane, 2,2-di(tert-butylperoxy)octane, 2,5-dimethylhexane-2,5-dihydroperoxide, 2,5-dimethyl-2,5-di(benzoylperoxy)hexane, 2,5-dimethyl-2,5-di (tert-butylperoxy)hexane, 2,5-dimethyl-2,5-di(tert-butylperoxy)hex-3-yne, 1,4-di(tert-butylperoxyisopropyl)benzene1,3-di(tert-butylperoxyisopropyl)benzene, di(tert-butylperoxy) isophthalate, performic acid, peracetic acid, perpropionic acid, perbutyric acid, perisovaleric acid, per-heptanoic acid, perbenzoic acid, m-chloroperbenzoic acid, monoperphthalic acid, p-methoxperbenzoic acid, m-nitroperbenzoic acid, α-pernaphthoic acid, β-pernaphthoic acid, di(trimethylsilyl) peroxide, trimethylsilyl triphenylsilyl peroxide, and combination thereof. In some embodiments, the oxidant comprises m-chloroperbenzoic acid (MCPBA), and in some embodiments, the oxidant comprises hydrogen peroxide.

The method can optionally be conducted in the presence of a solvent. As reported in Example 1, practical factors including cost, health hazard, solubility of the 2-allylphenol, oxidant, and solubility of the catalyst, and boiling point can be considered in selecting a solvent. For example, the solvent can be a non-polar solvent, for example benzene, toluene, ethylbenzene, cumene, xylenes, mesitylene, tetralin, chlorobenzene, dichlorobenzenes, chloroform, or combination thereof. The solvent can also be a polar solvent, for example water, methanol, ethanol, 2-propanol, acetone, methyl ethyl ketone, dimethyoxyethane, tetrahydrofuran, 1,4-dioxane, dimethyl formamide, dimethyl sulfoxide, acetonitrile, or combination thereof. Any combination of the foregoing solvents, including combinations of polar and non-polar solvents, can also be used. Methanol or 2-propanol are advantageous due to ease of removal from product by distillation, miscibility with aqueous hydrogen peroxide, and low cost. Thus in some embodiments, the solvent comprises methanol, 2-propanol, or combination thereof. The solvent can also be water. Toluene and chloroform are advantageous due to being good solvents for the 2-allylphenol and 2-(2,3-epoxypropyl)phenol, and poor solvents for the catalysts, thus simplifying catalyst removal and product isolation. Thus in some embodiments, the solvent comprises toluene, chloroform, or combination thereof.

The epoxidation can be done in a wide range of temperatures and times, which depend in part on the specific oxidant and catalyst used. As used herein, the terms, "epoxidation" and "reaction" both refer to the present method of making a 2-(2,3-epoxypropyl)phenol from a 2-allylphenol in the presence of an oxidant and catalyst. The reaction temperature is a balance between reaction time and oxidant decomposition rates. If the temperature is too low, the reaction will take too long. If the reaction temperature is too high, the oxidant will decompose before it has a chance to react with the 2-allylphenol. In order to achieve an economically feasible reaction time, the minimum reaction temperature can be −20, 0, or 20° C. The maximum temperature is determined in part by the decomposition temperature of the oxidant. For example, m-chloroperbenzoic acid begins to decompose at about 80° C. For some oxidants, including m-chloroperbenzoic acid, the reaction temperature can be −20 to 80° C., specifically 0 to 60° C., and more specifically 20 to 40° C. Hydrogen peroxide begins to decompose at about 40° C. Thus when hydrogen peroxide is used as the oxidant, the reaction temperature can be −20 to 50° C., specifically 0 to 45° C., and more specifically 20 to 40° C. The reaction time can be 10 minutes to 8 hours, specifically 20 minutes to 6 hours, and more specifically 30 minutes to 4 hours. In some embodiments, the reaction temperature is −10 to 50° C., and the reaction time is 10 minutes to 6 hours.

Figure 5:
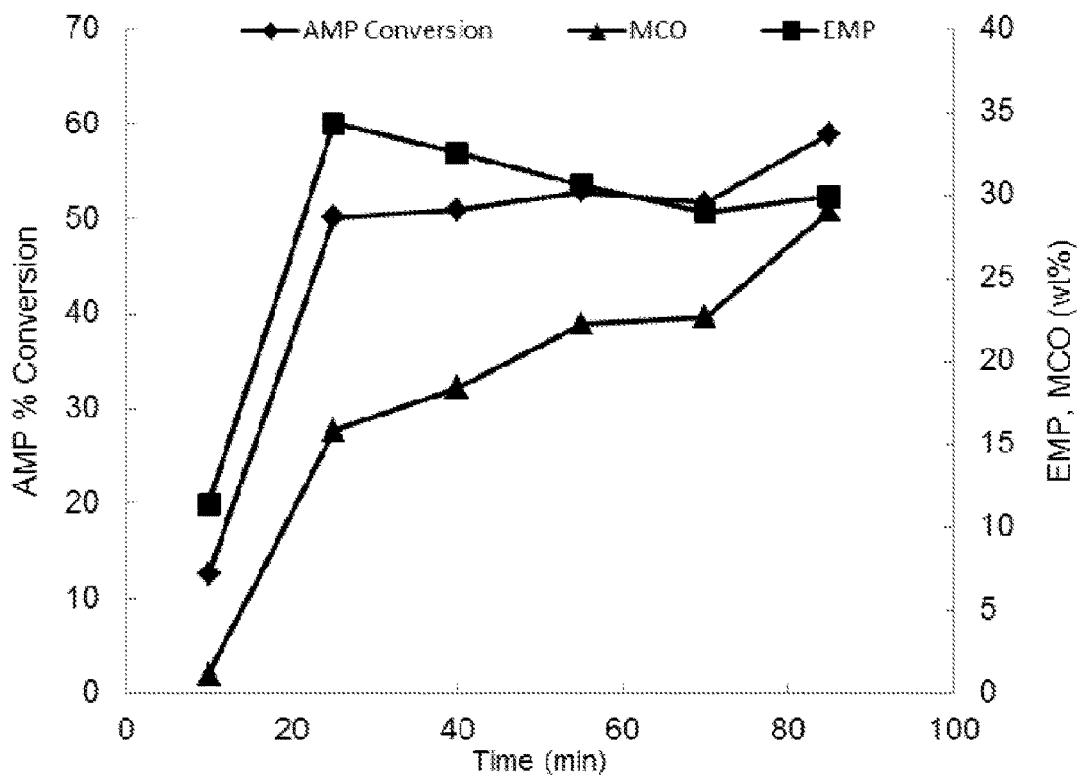
FIG. 5 depicts the percent conversion of 2-allyl-6-methylphenol, and amounts of 2-(2,3-epoxypropyl)-6-methylphenol and 8-methyl-3-chromanol in weight percent, plotted as a function of reaction time in the $MoO_2(acac)_2$-catalyzed epoxidation of 2-allyl-6-methylphenol with m-chloroperbenzoic acid of Example 15.
Figure 6:
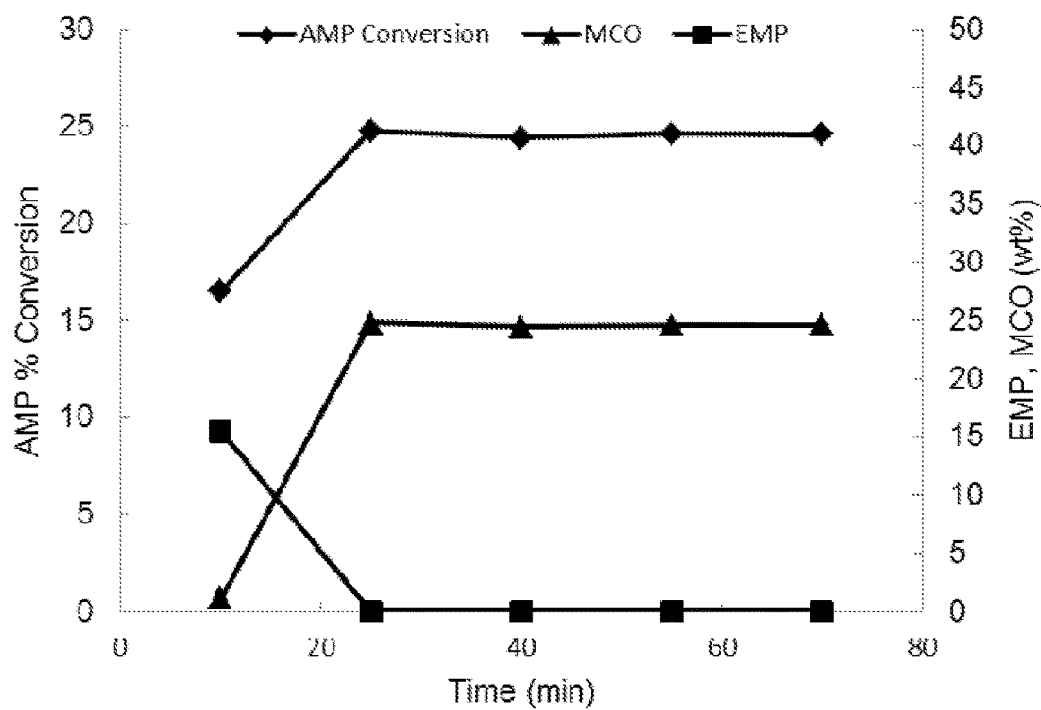
FIG. 6 depicts the percent conversion of 2-allyl-6-methylphenol, and amounts of 2-(2,3-epoxypropyl)-6-methylphenol and 8-methyl-3-chromanol in weight percent, plotted as a function of reaction time in the $MoO_2Cl_2$-catalyzed epoxidation of 2-allyl-6-methylphenol with m-chloroperbenzoic acid of Example 16.
Figure 7:
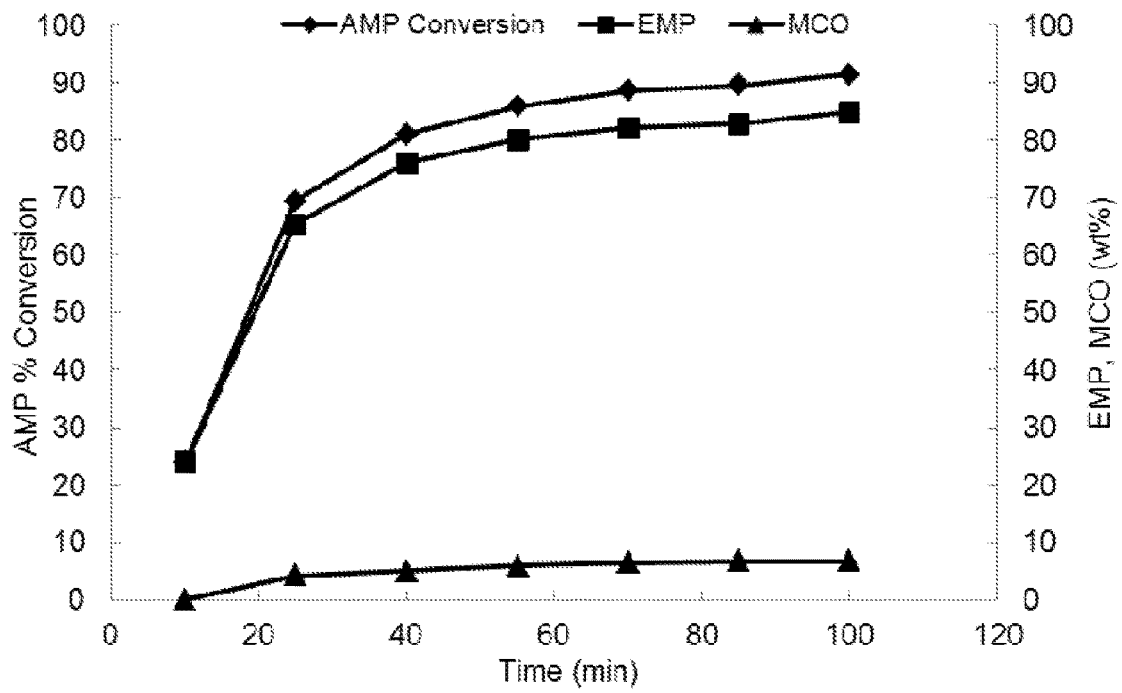
FIG. 7 depicts the percent conversion of 2-allyl-6-methylphenol, and amounts of 2-(2,3-epoxypropyl)-6-methylphenol and 8-methyl-3-chromanol in weight percent, plotted as a function of reaction time in the $H_2WO_4$-catalyzed epoxidation of 2-allyl-6-methylphenol with m-chloroperbenzoic acid of Example 17.
Figure 8:
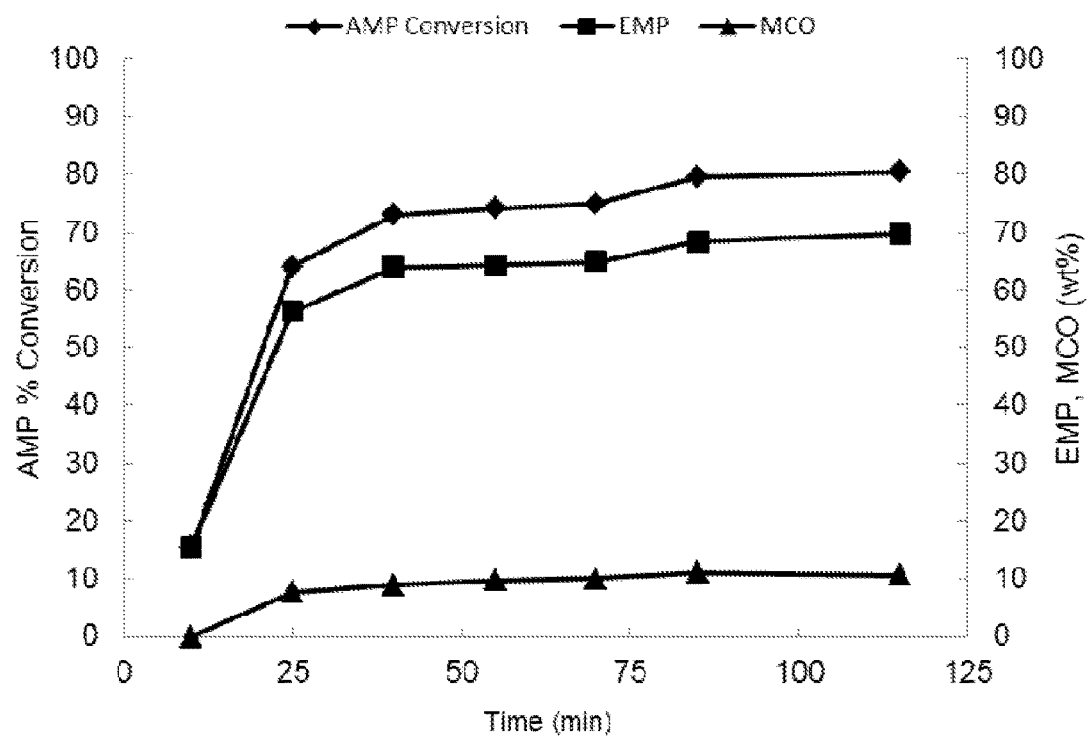
FIG. 8 depicts the percent conversion of 2-allyl-6-methylphenol, and amounts of 2-(2,3-epoxypropyl)-6-methylphenol and 8-methyl-3-chromanol, plotted as a function of reaction time in the $W(CO)_6$-catalyzed epoxidation of 2-allyl-6-methylphenol with m-chloroperbenzoic acid of Example 18.

At any reaction temperature, the percent conversion depends upon the oxidant, the activity of the catalyst, and the reaction time. For example, with m-chloroperbenzoic acid as the oxidant and a molybdenum catalyst such as $MoO_2(acac)_2$ and $MoO_2Cl_2$, 50% conversion of 2-allylphenol occurs in the first ten minutes (FIGS. 5 and 6). With m-chloroperbenzoic acid as the oxidant and a tungsten catalyst such as $H_2WO_4$ and $W(CO)_6$, 60% of the 2-allylphenol conversion occurs in the first 30 minutes with another 20% conversion occurring in 70 minutes more (FIGS. 7 and 8). In some embodiments, there is 50 to 100% conversion of the 2-allylphenol in 10 minutes to 6 hours at a reaction temperature of −10 to 50° C.

In some embodiments, the 2-allylphenol comprises 2-allyl-6-methylphenol and the 2-(2,3-epoxypropyl)phenol comprises 2-(2,3-epoxypropyl)-6-methylphenol. A method of making 2-(2,3-epoxypropyl)-6-methylphenol comprises reacting 2-allyl-6-methylphenol with an oxidant comprising m-chloroperbenzoic acid in the presence of a catalyst comprising bis(acetylacetonate)dioxomolybdenum (VI), tungstic acid, tungsten hexacarbonyl, or combination thereof.

In the epoxidation reaction, a 3-chromanol of structure

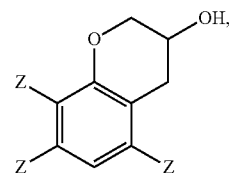

wherein each Z is independently defined as it is for the 2-allylphenol and the 2-(2,3-epoxypropyl)phenol, can be formed. Thus mixtures of 2-(2,3-epoxypropyl)phenol and 3-chromanol can be formed. In some embodiments, the composition comprises 0 to 40 weight percent, specifically 1 to 40 weight percent, and more specifically 1 to 20 weight percent, of the 3-chromanol, based on the total weight of the composition. Moreover, if the conversion of the 2-allylphenol is incomplete, mixtures of 2-allylphenol, 2-(2,3-epoxypropyl)phenol, and 3-chromanol can be formed. Thus in some embodiments, the reaction of 2-allylphenol with an oxidant in the presence of a catalyst can produce a composition comprising, based on the total amount of the composition, 1 to 90 weight percent of a 2-(2,3-epoxypropyl)phenol of structure

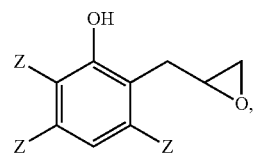

5 to 90 weight percent of a 2-allylphenol of structure

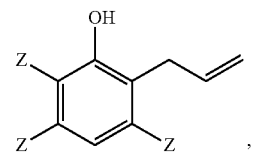

and 0 to 40 weight percent of a 3-chromanol of structure

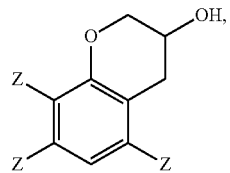

wherein each occurrence of Z is independently hydrogen, halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, or $C_2$-$C_{12}$ halohydrocarbyloxy wherein at least two carbon atoms separate the halogen and oxygen atoms; and wherein all weight percents are based on the total weight of the 2-(2,3-epoxypropyl)phenol, the 2-allylphenol, and the 3-chromanol.

In some embodiments, the 2-(2,3-epoxypropyl)phenol comprises 2-(2,3-epoxypropyl)-6-methylphenol, the 2-allylphenol comprises 2-allyl-6-methylphenol, and the 3-chromanol comprises

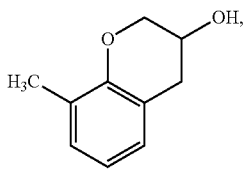

which is referred to herein as "8-methyl-3-chromanol", or "MCO". The composition can comprise 0 to 40 weight percent, specifically 1 to 40 weight percent, and more specifically 1 to 20 weight percent 8-methyl-3-chromanol, based on the total weight of the composition. Thus, in some embodiments, the composition comprises 1 to 90 weight percent 2-(2,3-epoxypropyl)-6-methylphenol, 5 to 90 weight percent 2-allyl-6-methylphenol, and 0 to 40 weight percent 8-methyl-3-chromanol, based on the total weight of the composition.

Depending upon the catalyst, the amount of 2-(2,3-epoxypropyl)phenol produced can decrease with time as a result of a secondary cyclization reaction which results in the formation of a 3-chromanol from 2-allylphenol. For example, as can be seen from FIG. 5, when the 2-allylphenol is 2-allyl-6-methylphenol, the oxidant is m-chloroperbenzoic acid, and the catalyst is $MoO_2(acac)_2$, a maximum 2-(2,3-epoxypropyl)-6-methylphenol amount of about 35 weight percent was obtained in the first 20 min of the reaction. The final 2-(2,3-epoxypropyl)-6-methylphenol amount was about 30 weight percent. Thus in some embodiments, the composition comprises 1 to 40 weight percent 2-(2,3-epoxypropyl)-6-methylphenol, 30 to 90 weight percent 2-allyl-6-methylphenol, and 1 to 40 weight percent 8-methyl-3-chromanol, based on the total weight of the 2-(2,3-epoxypropyl)-6-methylphenol, 2-allyl-6-methylphenol, and 8-methyl-3-chromanol. As can be seen from FIG. 6, with $MoO_2Cl_2$ the maximum 2-(2,3-epoxypropyl)-6-methylphenol amount was 15 weight percent, obtained in 10 minutes. After about 22 minutes, no 2-(2,3-epoxypropyl)-6-methylphenol was observed, but 25 weight percent 8-methyl-3-chromanol formed. As can be seen from FIG. 7, with $H_2WO_4$, 65 weight percent 2-(2,3-epoxypropyl)-6-methylphenol was obtained in the first 20 min, and 85 weight percent 2-(2,3-epoxypropyl)-6-methylphenol was obtained after an additional 80 minutes. As can be seen from FIG. 8, the results with $W(CO)_6$ were similar to the results with $H_2WO_4$. Thus in some embodiments, the composition comprises 5 to 90 weight percent 2-(2,3-epoxypropyl)-6-methylphenol, 5 to 90 weight percent 2-allyl-6-methylphenol, and 1 to 20 weight percent 8-methyl-3-chromanol, based on the total weight of the composition, based on the total weight of the 2-(2,3-epoxypropyl)-6-methylphenol, the 2-allyl-6-methylphenol, and the 8-methyl-3-chromanol.

Under some conditions, reaction of a 2-allylphenol, for example 2-allyl-6-methylphenol, with an oxidant in the presence of a catalyst can result in the formation of a thermoset polymer. The thermoset polymer can have a glass transition temperature of 230 to 260° C., specifically 230 to 250° C., and more specifically 235 to 245° C. In particular, reaction of 2-allyl-6-methylphenol with an oxidant in the presence of a catalyst can result in a thermoset polymer having a glass transition temperature of 235 to 245° C. For example, reaction of 2-allyl-6-methylphenol with aqueous hydrogen peroxide in the presence of $MoO_2(acac)_2$ and methanol, as in Ex. 4, followed by heating at 30 to 65° C., as in Ex. 19, produced a thermoset polymer having a glass transition temperature of 241° C.

This invention includes at least the following embodiments.

Embodiment 1: A method of making a 2-(2,3-epoxypropyl)phenol, comprising reacting a 2-allylphenol with an oxidant in the presence of a catalyst; wherein the 2-allylphenol comprises

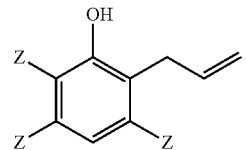

and the 2-(2,3-epoxypropyl)phenol comprises

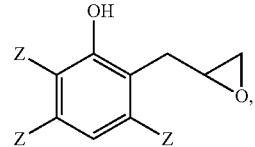

wherein each occurrence of Z is independently hydrogen, halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, or $C_2$-$C_{12}$ halohydrocarbyloxy wherein at least two carbon atoms separate the halogen and oxygen atoms.

Embodiment 2: The method of embodiment 1, wherein the 2-allylphenol comprises 2-allyl-6-methylphenol and the 2-(2,3-epoxypropyl)phenol comprises 2-(2,3-epoxypropyl)-6-methylphenol.

Embodiment 3: The method of embodiments 1 or 2, wherein the catalyst is a transition metal catalyst comprising molybdenum, vanadium, tungsten, titanium, manganese, niobium, or combination thereof.

Embodiment 4: The method of any of embodiments 1-3, wherein the catalyst comprises bis(acetylacetonato)dioxomolybdenum (VI), molybdenum dichloride dioxide, tungstic acid, tungsten hexacarbonyl, or combination thereof.

Embodiment 5: The method of any of embodiments 1-4, wherein the oxidant comprises hydrogen peroxide, an alkyl peroxide, an alkyl hydroperoxide, a ketone peroxide, a diacyl peroxide, a diperoxy ketal, a peroxyester, a peroxydicarbonate, a peroxy acid, a perbenzoic acid, or combination thereof.

Embodiment 6: The method of any of embodiments 1-5, wherein the oxidant comprises m-chloroperbenzoic acid.

Embodiment 7: The method of any of embodiments 1-6, wherein the oxidant comprises hydrogen peroxide.

Embodiment 8: The method of any of embodiments 1-7, wherein reaction temperature is −10 to 50° C., and reaction time is 10 minutes to 6 hours.

Embodiment 9: The method of any of embodiments 1-8, wherein there is 50 to 100% conversion of the 2-allylphenol in 10 minutes to 6 hours at a reaction temperature of −10 to 50° C.

Embodiment 10: The method of any of embodiments 1-9, wherein there is 50 to 100% selectivity for 2-(2,3-epoxypropyl)phenol.

Embodiment 11: The method of any of embodiments 1-10, wherein a 3-chromanol of structure

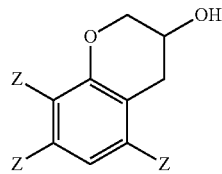

is made along with the 2-(2,3-epoxypropyl)phenol, wherein Z is defined as in embodiment 1.

Embodiment 12: The method of any of embodiments 1-11, wherein: the 2-allylphenol comprises 2-allyl-6-methylphenol; the 2-(2,3-epoxypropyl)phenol comprises 2-(2,3-epoxypropyl)-6-methylphenol; the oxidant comprises m-chloroperbenzoic acid; and the catalyst comprises bis(acetylacetonate)dioxomolybdenum (VI), tungstic acid, tungsten hexacarbonyl, or combination thereof.

Embodiment 12a: A method of making 2-(2,3-epoxypropyl)-6-methylphenol, comprising reacting 2-allyl-6-methylphenol with an oxidant comprising m-chloroperbenzoic acid in the presence of a catalyst comprising bis(acetylacetonate)dioxomolybdenum (VI), tungstic acid, tungsten hexacarbonyl, or combination thereof.

Embodiment 13: A composition comprising: 1 to 90 weight percent of a 2-(2,3-epoxypropyl)phenol of structure

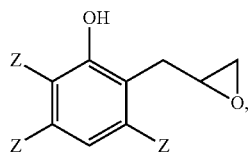

5 to 90 weight percent of a 2-allylphenol of structure

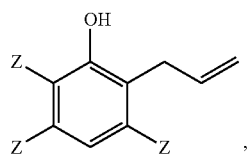

and 0 to 40 weight percent of a 3-chromanol of structure

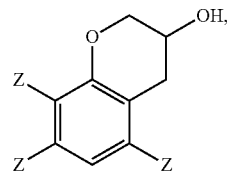

wherein each occurrence of Z is independently hydrogen, halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, or $C_2$-$C_{12}$ halohydrocarbyloxy wherein at least two carbon atoms separate the halogen and oxygen atoms, and wherein all weight percents are based on the total weight of the 2-(2,3-epoxypropyl)phenol, 2-allylphenol, and 3-chromanol.

Embodiment 14: The composition of embodiment 13, wherein the 2-(2,3-epoxypropyl)phenol comprises 2-(2,3-epoxypropyl)-6-methylphenol, the 2-allylphenol comprises 2-allyl-6-methylphenol, and the 3-chromanol comprises 8-methyl-3-chromanol.

Embodiment 15: The composition of embodiments 13 or 14, comprising 1 to 40 weight percent 2-(2,3-epoxypropyl)-6-methylphenol, 30 to 90 weight percent 2-allyl-6-methylphenol, and 1 to 40 weight percent 8-methyl-3-chromanol, based on the total weight of the 2-(2,3-epoxypropyl)-6-methylphenol, 2-allyl-6-methylphenol, and 8-methyl-3-chromanol.

Embodiment 16: The composition of embodiment 13, comprising 5 to 90 weight percent 2-(2,3-epoxypropyl)-6-methylphenol, 5 to 90 weight percent 2-allyl-6-methylphenol, and 1 to 20 weight percent 8-methyl-3-chromanol, based on the total weight of the 2-(2,3-epoxypropyl)-6-methylphenol, 2-allyl-6-methylphenol, and 8-methyl-3-chromanol.

Embodiment 17: A thermoset polymer made by reacting a 2-allylphenol of structure

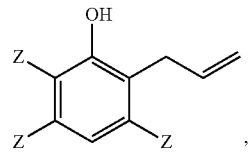

wherein each occurrence of Z is independently hydrogen, halogen, unsubstituted or substituted $C_1$-$C_{12}$ hydrocarbyl provided that the hydrocarbyl group is not tertiary hydrocarbyl, $C_1$-$C_{12}$ hydrocarbylthio, $C_1$-$C_{12}$ hydrocarbyloxy, or $C_2$-$C_{12}$ halohydrocarbyloxy wherein at least two carbon atoms separate the halogen and oxygen atoms, with an oxidant in the presence of a catalyst.

Embodiment 18: The thermoset polymer of embodiment 17, wherein the 2-allylphenol comprises 2-allyl-6-methylphenol, and the thermoset polymer has a glass transition temperature of 235 to 245° C.

This invention is further illustrated by the following non-limiting examples.

EXAMPLES

The materials utilized in the examples are listed below in Table 1.

TABLE 1

Materials

| CAS Number | Chemical Name | Purity (wt %) | Abbreviations |
|---|---|---|---|
| 3354-58-3 | 2-Allyl-6-methylphenol | 50% | AMP |
| 1567906-11-9 | 2-(2,3-Epoxypropyl)-6-methylphenol | Variable | EMP |
| 136514-01-7 | 8-Methyl-3-chromanol | Variable | MCO |
| 7722-84-1 | Aqueous $H_2O_2/H_2O$ | 50% | — |
| 75-05-8 | Acetonitrile | >99.9% | — |
| 67-66-3 | Chloroform | >99.9% | — |
| 865-49-6 | Chloroform-d | 99.8% | $CDCl_3$ |
| 68-12-2 | N,N-Dimethylformamide | >99.9% | DMF |
| 123-91-1 | 1,4-Dioxane | >99% | — |
| 67-56-1 | Methanol | 99% | — |
| 78-93-3 | Methyl Ethyl Ketone | >99% | MEK |
| 109-99-9 | Tetrahydrofuran | >99.9% | THF |
| 108-88-3 | Toluene | 99% | — |
| 937-14-4 | m-chloroperbenzoic acid | 77% | MCPBA |
| 63393-96-4 | Trioctylmonomethyl ammonium chloride | 99% | ALIQUAT ™ 336 |
| 139-13-9 | 2,2',2''-Nitrilotriacetic acid | — | NTA |
| 13939-06-5 | Molybdenum Hexacarbonyl | 99.9% | — |
| 17524-05-9 | Bis(acetylacetonato)dioxomolybdenum (VI) | — | $MoO_2(acac)_2$ |
| 13637-68-8 | Molybdenum dichloride dioxide | — | $MoO_2Cl_2$ |
| 14040-11-0 | Tungstic acid hydrate | 97% | $H_2WO_4$ |
| 7783-03-1 | Tungsten hexacarbonyl | 99% | $W(CO)_6$ |
| 12027-43-9 | Tungstosilicic Acid | 99.9% | $H_4O_{40}SiW_{12}\cdot xH_2O$ |
| 13476-99-8 | Vanadium acetylacetonate | 97% | $V(acac)_2$ |
| 3153-26-2 | Vanadyl acetylacetonate | 98% | $VO(acac)_2$ |
| 1314-62-1 | Vanadium pentoxide | — | $V_2O_5$ |

Figure 2:
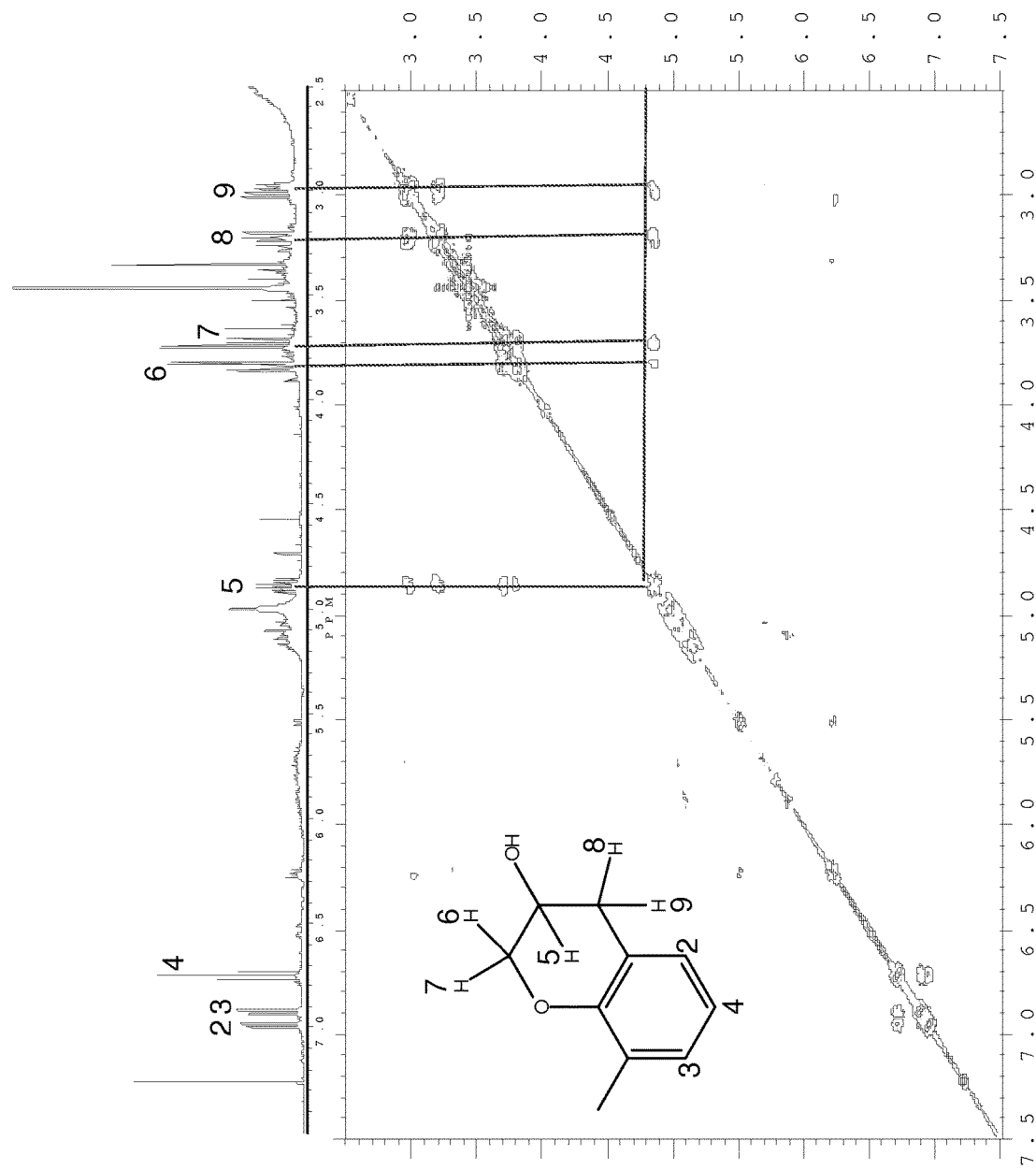
FIG. 2 depicts the 400 Mhz $^1$H-NMR spectrum and 2D-correlation (COSY) spectrum of the reaction mixture of Example 3, which is the product of the reaction of 2-allyl-6-methylphenol with m-chloroperbenzoic acid in the presence of $MoO_2(acac)_2$ after 5 hours at 30° C.
Figure 3:
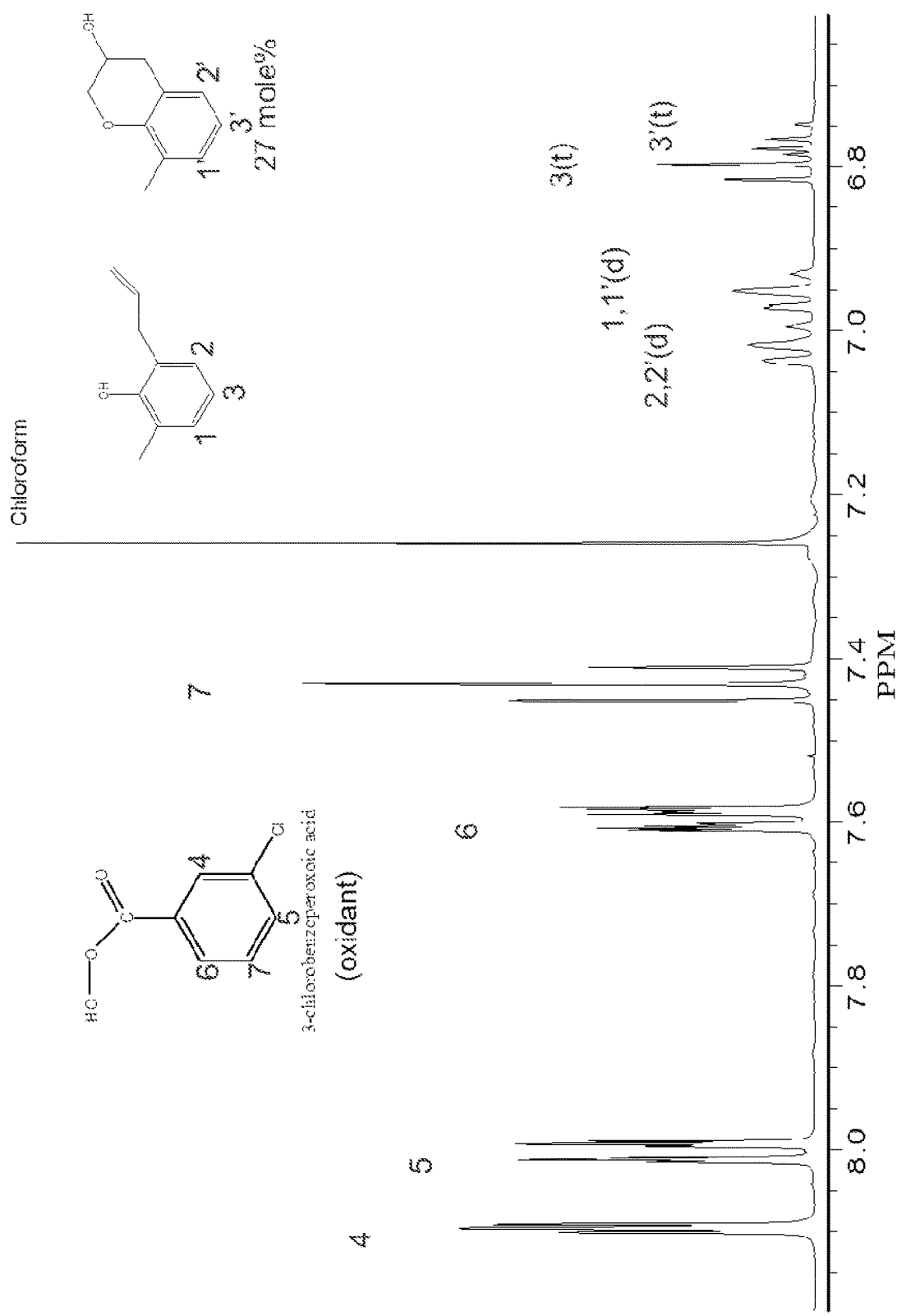
FIG. 3 depicts the 400 Mhz $^1$H-NMR spectrum in the range of 8.2-6.8 ppm of the reaction mixture of Example 3.
Figure 4:
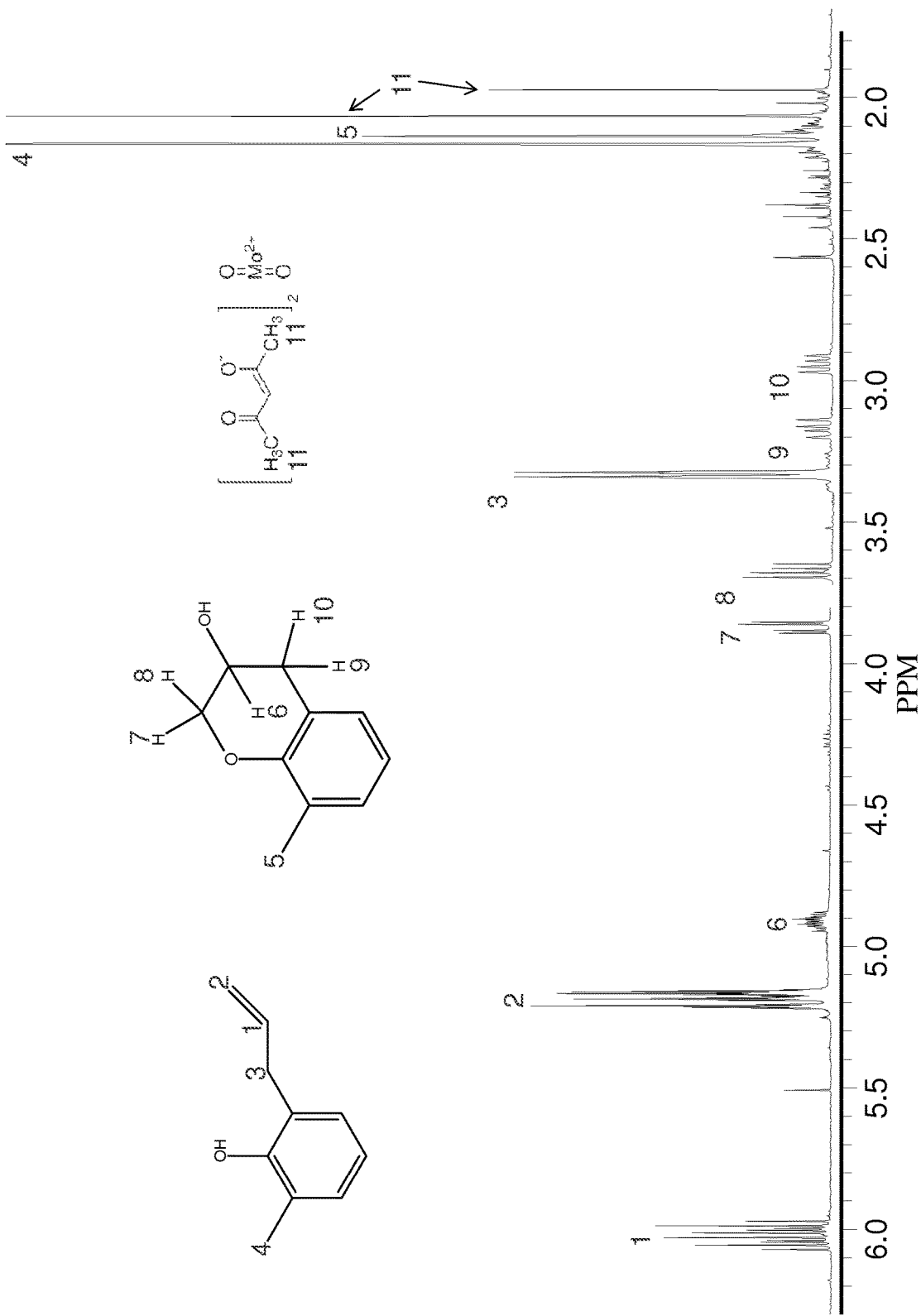
FIG. 4 depicts the 400 Mhz $^1$H-NMR spectrum in the range of 6-2 ppm of the reaction product of Example 3.

The reaction mixtures were characterized by $^1$H-NMR spectroscopy. The $^1$H-NMR spectra of reaction mixtures are depicted in FIGS. 1 to 4. In FIGS. 2 to 4, the $^1$H-NMR peaks are identified by numbers corresponding to specific hydrogen atoms in the chemical structures therein as indicated.

Example 1

Solvent Screening

Observations on the solubility of 50 wt % $H_2O2/H_2O$ and AMP in various solvents are summarized in Table 2. All solubility studies were performed at room temperature and atmospheric pressure. The oxidant (aqueous $H_2O_2$) and solute (AMP) were mixed with the solvents listed in Table 2 and observations were recorded. $H_2O_2$ and AMP were found to be completely miscible in polar solvents. AMP is soluble in aromatic solvents whereas aqueous $H_2O_2$ is insoluble, resulting in the formation of two phases. In order to compare the solvents, cost, health hazard, $H_2O_2$ and AMP solubility, catalyst solubility, and ease of solvent separation based on boiling point were assigned positive (+) or negative (−) weights. The results are summarized in Table 3. This exercise identified methanol as a potential solvent. Methanol is relatively inexpensive and non-hazardous compared to the other solvents evaluated. Further, the low boiling point of methanol makes its separation and recovery less energy intensive than the other solvents. All the catalyst candidates except tungstic acid were found to be insoluble in methanol and thus can be recovered by filtration. Tungstic acid was sparingly soluble in methanol.

TABLE 2

Solubility of 50% $H_2O_2/H_2O$ and 2-allyl-6-methyl phenol in various solvents

| System | Remarks |
|---|---|
| Methanol | Homogeneous single phase was observed. |
| Toluene | Test 1: Toluene and $H_2O_2$ were immiscible—two phases were observed. Two phases were observed despite the introduction of phase transfer catalyst (20 wt % NTA in $H_2O$). Test 2: ALIQUAT ™ 336, a phase transfer catalyst, was evaluated by adding it to a mixture of toluene + $H_2O_2$. Two phases were observed. Addition of AMP to the above mixture resulted in the solution turning green over time (indicative of possible reaction). |
| Acetonitrile | Homogeneous single phase was observed. |
| 2-Propanol | Homogeneous single phase was observed. |
| MEK$^a$ | MEK and $H_2O_2$ formed a milky suspension. Solid agglomerate was observed after a few minutes. This was attributed to solubility of poly(acrylonitrile-butadiene-styrene) from the pipette used to transfer solvent in MEK. The test was repeated with glass pipettes. A milky suspension was again observed indicating some form of adverse reaction between MEK and $H_2O_2$. AMP was not added to the mixture. |

TABLE 2-continued

Solubility of 50% $H_2O_2/H_2O$ and 2-allyl-6-methyl phenol in various solvents

| System | Remarks |
|---|---|
| Acetone | Homogeneous single phase was observed. |
| DMF | Homogeneous single phase was observed. |
| Ethanol | Homogeneous single phase was observed. |
| THF | Homogeneous single phase was observed. |
| 1,4-Dioxane | Homogeneous single phase was observed. |
| Chloroform | $CHCl_3$ and $H_2O_2$ were immiscible. Two phases were observed. Phase transfer catalyst may enhance the contact between the two phases. |

[a]Dissolved poly(acrylonitrile-butadiene-styrene) from pipettes.

TABLE 3

Criteria adopted for the selection of solvent

| Solvent | Cost[b] US$/liter | Hazard (HMIS)[c] | $H_2O_2$/AMP Solubility | Catalyst Solubility[d] | Solvent Separation (bp ° C.) |
|---|---|---|---|---|---|
| Methanol | +(45) | +(1) | + | + | +(64.7) |
| Toluene | +(63) | −(3) | − | + | −(110) |
| Acetonitrile | −(143) | −(3) | + | + | −(81) |
| 2-Propanol | +(61) | −(2) | + | + | −(82) |
| MEK[a] | −(77) | −(2) | − | + | −(80) |
| Acetone | −(75) | −(2) | + | + | +(56) |
| DMF | −(109) | −(2) | + | + | −(102) |
| Ethanol | −(95) | −(2) | + | + | −(78) |
| THF | −(85) | −(2) | + | + | +(65) |
| 1,4-Dioxane | −(147) | −(2) | + | + | −(100) |
| Chloroform | −(88) | −(2) | − | + | +(60.5) |

[a]Dissolved poly(acrylonitrile-butadiene-styrene) from pipettes.
[b]Cost estimates are qualitative and based on procurement of CHROMASOLV™ grade solvents in small quantities. The pricing information was obtained from Sigma-Aldrich. Prices above US$70 per liter were considered undesirable.
[c]HMIS health hazard of 2 or greater was considered undesirable.
[d]A "+" indicates the catalyst was insoluble. Insolubility of catalyst to form a heterogeneous reaction mixture eliminates catalyst separation issues.

Example 2

Aqueous $H_2O_2$ and $MoO_2(Acac)_2$-Catalyzed Epoxidation of 2-Allyl-6-Methylphenol The reaction mixture (AMP+$H_2O_2$+$CH_3OH$+$MoO_2$(acac)$_2$) was initially colorless and turned dark brown within the first half hour of the reaction. This color change may be attributed to the formation of molybdenum diperoxo species (resulting in a change of the molybdenum oxidation state). The results obtained were strongly dependent upon reaction temperature. At low reaction temperatures of 15-20° C. the signal intensity of AMP (measured by GC/MS, peak height of AMP by GC) was found to be similar for both the initial and final samples, suggesting absence of reaction at these temperatures. On the other hand, a significant reduction in peak area for the AMP peak (confirmed with GC/MS and $^1$H-NMR) was observed at the higher temperature of 40° C.

The mass of the product ion estimated theoretically and that obtained by the GC/MS analysis of the reaction mixture was consistent with formation of EMP. The non-availability of an EMP external standard and the absence of a model MS spectrum for EMP in the instrument database and open literature reduced the confidence of the chemical structure predicted by the MS software. Further, the identical exact masses for epoxidized AMP (EMP) and cyclized AMP (8-methyl-3-chromanol) eliminated the use of MS to differentiate between these reaction products.

FIG. 1 depicts the $^1$H-NMR spectrum of the reaction mixture form Ex. 4, which contains unreacted AMP, methanol, 8-methyl-3-chromanol. As can be seen from FIG. 1, the reduction in intensity of the absorption peaks at 7 ppm (doublets) and 6.7 ppm (triplets), indicated by "1" in the figure, compared to the same peaks in the $^1$H-NMR spectrum of unreacted AMP, suggests that reaction of the carbon-carbon double bond of AMP has taken place. The busy $^1$H-NMR spectrum coupled with an overbearing absorption peak from the methanol hindered the identification of EMP by $^1$H-NMR. The sample needed to be cleaned by removal of methanol and residual hydrogen peroxide prior to analysis.

Similar results, reduction in the intensity of the absorption peaks corresponding to the carbon-carbon double bond and the formation of additional peaks, were obtained when both W-based and other Mo-based catalysts were used for the epoxidation reaction. Thus reaction of the carbon-carbon double bond of AMP has been proven.

Examples 3-14

Metal-Catalyzed Epoxidation of 2-Allyl-6-Methylphenol

The issues associated with the identification of the reaction products in Ex. 2 were eliminated by conducting the AMP epoxidation reaction in $CDCl_3$ instead of methanol. The use of $CDCl_3$ eliminated the need for solvent separation thereby enabling conclusive identification of the products by NMR without heating or otherwise concentrating the sample. MCPBA was used as an alternative to $H_2O_2$ due to the immiscibility of $H_2O_2$ with chloroform. The time required for sample preparation was also minimized by performing the catalyst screening studies in $CDCl_3$ instead of methanol or chloroform.

The metal-catalyzed epoxidation of AMP using MCPBA or $H_2O_2$ was studied to identify the best catalyst for selective formation of EMP. The reactants and results for Ex. 3-13 are summarized in Table 4. Most of the catalyst studies were performed using the following reactants: AMP+MCPBA+catalyst. In Examples 4, 9, and 11, $H_2O_2$ was substituted for MCPBA. The solvent was $CDCl_3$ in Ex. 1, 3-10, and 12-14. In Ex. 4 and 11, methanol was substituted for $CDCl_3$.

The initial composition of the reaction mixtures was $5.02 \times 10^{-3}$ mol AMP+$8.6 \times 10^{-3}$ mol oxidant+0.18 mol solvent. The oxidants used were MCPBA in $CDCl_3$ and 50 wt % $H_2O_2/H_2O$ in methanol or $CDCl_3$. The reactions were conducted at 25° C. for 6 h. The percent conversion of AMP (column 3) and amount and selectivity for EMP (column 4) and 8-methyl-3-chromanol (column 5) in the reaction of AMP with MCPBA or 50 wt % $H_2O_2/H_2O$ and various metal catalysts are summarized in Table 4. A temperature exotherm was observed in Ex. 4, 9, and 11, where the oxidant was 50 wt % $H_2O_2/H_2O$. When a vanadium catalyst was used in combination with 50 wt % $H_2O_2/H_2O$, highly exothermic decomposition of the $H_2O_2$ was observed when the catalyst was introduced into the reaction mixture. Exothermic hydrogen $H_2O_2$ decomposition was even observed at very low vanadium catalyst loadings. MCPBA was soluble in $CDCl_3$ whereas the by-product of the reaction, m-chloroperbenzoic acid formed after the transfer of an oxygen atom to AMP, was insoluble. Thus, the formation of insoluble solid in epoxidation with MCPBA serves as an indirect indication of reaction. The absence of MCPBA decomposition in the presence of catalyst, was confirmed in separate tests.

$^1$H-NMR spectra of the product mixture obtained after the epoxidation of AMP with MCPBA in the presence of metal catalysts in CDCl$_3$ were relatively clean compared to the NMR spectra of the reaction product obtained in methanol. The formation of EMP in Ex. 5 and 8 was confirmed by $^1$H-NMR spectroscopy. The reaction mixtures were also studied by 2D-correlation spectroscopy (COSY). An exemplary COSY spectrum of a reaction mixture is reproduced in FIG. 2. The presence of 8-methyl-3-chromanol was identified from the COSY spectrum. The formation of 8-methyl-3-chromanol is an intramolecular cyclization reaction, and can be attributed to reaction between the phenolic hydroxyl and epoxide groups of EMP. The identification of which absorption peaks in the $^1$H-NMR spectra of the reaction product corresponded to the 8-methyl-3-chromanol was done with the aid of COSY spectroscopy. Once the 8-methyl-3-chromanol peaks were identified, standard $^1$H-NMR spectroscopy was used to quantify the amount of 8-methyl-3-chromanol in reaction products in the catalyst screening studies summarized in Table 4. The carbon-carbon double bond present in the allylic side chain of AMP underwent epoxidation resulting in the formation of EMP. The 8-methyl-3-chromanol could be formed by intramolecular cyclization of EMP. Thus, the formation of 8-methyl-3-chromanol suggests the formation of EMP, at least as an intermediate. The nearly complete selectivity toward 8-methyl-3-chromanol as determined by $^1$H-NMR spectroscopy suggests that long reaction times are conducive to cyclization of EMP. In addition long reaction times, the facile formation of 8-methyl-3-chromanol can also be attributed to high reactivity of the epoxide group and absence of steric hindrance to formation of the chromane ring.

Example 3

MCPBA and MoO$_2$(Acac)$_2$ Catalyst 0.75 mL of AMP, 1.5 g of MCPBA, 400 mg of MoO$_2$(acac)$_2$, and CDCl$_3$ were charged into a vessel. The vessel was cooled by placing it in an ice bath. The mixture was agitated with a magnetic stir bar. The reaction mixture was analyzed by $^1$H-NMR after stirring at 25° C. for 6 h.

Example 4

Aqueous H$_2$O$_2$ and MoO$_2$(Acac)$_2$ Catalyst 3 mL of AMP, 4 mL of 50 wt % H$_2$O$_2$/H$_2$O, 400 mg of MoO$_2$(acac)$_2$, and methanol were charged into a vessel. The reaction was conducted under near ambient conditions and the mixture was agitated with a magnetic stir bar. The reaction mixture was analyzed by GC-MS after stirring at 25° C. for 6 h.

Example 5

MCPBA and MoO$_2$Cl$_2$ Catalyst 0.75 mL of AMP, 1.5 g of MCPBA, 400 mg of MoO$_2$Cl$_2$, and CDCl$_3$ were charged into a vessel. The vessel was cooled by placing it in an ice bath while the mixture was agitated with a magnetic stir bar. The reaction mixture was analyzed by $^1$H-NMR after stirring at 25° C. for 6 h.

Example 6

MCPBA and Mo(Co)$_6$ Catalyst 0.75 mL of AMP, 1.5 g of MCPBA, 400 mg of Mo(CO)$_6$, and CDCl$_3$ were charged into a vessel. The vessel was cooled by placing it in an ice bath while the mixture was agitated with a magnetic stir bar. The reaction mixture was analyzed by $^1$H-NMR after stirring at 25° C. for 6 h.

Example 7

MCPBA and H$_2$WO$_4$ Catalyst 0.75 mL of AMP, 1.5 g of MCPBA, 200 mg of H$_2$WO$_4$, and CDCl$_3$ were charged into a vessel. The vessel was cooled by placing it in an ice bath while the mixture was agitated with a magnetic stir bar. The reaction mixture was analyzed by $^1$H-NMR after stirring at 25° C. for 6 h.

Example 8

MCPBA and W(Co)$_6$ Catalyst 0.75 mL of AMP, 1.5 g of MCPBA, 200 mg of W(CO)$_6$, and CDCl$_3$ were charged into a vessel. The vessel was cooled by placing it in an ice bath while the mixture was agitated with a magnetic stir bar. The reaction mixture was analyzed by $^1$H-NMR after stirring at 25° C. for 6 h.

Example 9

Aqueous H$_2$O$_2$ and W(Co)$_6$ Catalyst 0.75 mL of AMP, 4 mL of 50 wt % H$_2$O$_2$/H$_2$O, 200 mg of W(CO)$_6$, and CDCl$_3$ were charged into a vessel. The vessel was cooled by placing it in an ice bath while the mixture was agitated with a magnetic stir bar. The reaction mixture was analyzed by $^1$H-NMR after stirring at 25° C. for 6 h.

Example 10

MCPBA and H$_4$O$_{40}$SiW$_{12}$.xH$_2$O Catalyst 0.75 mL of AMP, 1.5 g of MCPBA, 200 mg of H$_4$O$_{40}$SiW$_{12}$.xH$_2$O, and CDCl$_3$ were charged into a vessel. The vessel was cooled by placing it in an ice bath while the mixture was agitated with a magnetic stir bar. The reaction mixture was analyzed by $^1$H-NMR after stirring at 25° C. for 6 h.

Example 11

Aqueous H$_2$O$_2$ and H$_4$O$_{40}$SiW$_{12}$.xH$_2$O Catalyst 0.75 mL of AMP, 4 mL of 50 wt % H$_2$O$_2$/H$_2$O, 200 mg of H$_4$O$_{40}$SiW$_{12}$.xH$_2$O, and methanol were charged into a vessel. The vessel was cooled by placing it in an ice bath while the mixture was agitated with a magnetic stir bar. The reaction mixture was analyzed by $^1$H-NMR after stirring at 25° C. for 6 h.

Example 12

MCPBA and V(Acac)$_2$ Catalyst 0.75 mL of AMP, 1.5 g of MCPBA, 250 mg of V(acac)$_2$, and CDCl$_3$ were charged into a vessel. The vessel was cooled by placing it in an ice bath while the mixture was agitated with a magnetic stir bar. The reaction mixture was analyzed by $^1$H-NMR after stirring at 25° C. for 6 h.

Example 13

MCPBA and VO(Acac)$_2$ Catalyst 0.75 mL of AMP, 4 mL of 50 wt % $H_2O_2/H_2O$, 250 mg of VO(acac)$_2$, and CDCl$_3$ were charged into a vessel. The vessel was cooled by placing it in an ice bath while the mixture was agitated with a magnetic stir bar. The reaction mixture was analyzed by $^1$H-NMR after stirring at 25° C. for 6 h.

Example 14

MCPBA and V$_2$O$_5$ Catalyst 0.75 mL of AMP, 1.5 g of MCPBA and 250 mg of V$_2$O$_5$ were charged into a vessel. The vessel was cooled by placing it in an ice bath while the mixture was agitated with a magnetic stir bar. The reaction mixture was analyzed by $^1$H-NMR after stirring at 25° C. for 6 h.

TABLE 4

Percent conversion of AMP, and yields for EMP and MCO in the metal-catalyzed epoxidation of AMP

| Ex. | Catalyst | Oxidant | AMP (% Conv.) | EMP$^b$ (mol %) | MCO$^b$ (mol %) |
|---|---|---|---|---|---|
| 3 | MoO$_2$(acac)$_2$ | MCPBA | 21 | — | 21 (100) |
| 4 | MoO$_2$(acac)$_2$ | 50 wt % $H_2O_2/H_2O$ in CH$_3$OH | 27 | — | 27 (100) |
| 5 | MoO$_2$Cl$_2$ | MCPBA | 59.9 | 29 (48) | 29.9 (50) |
| 6 | Mo(CO)$_6$ | MCPBA | 0 | — | — |
| 7 | H$_2$WO$_4$ | MCPBA | 92.5 | — | 92.5 (100) |
| 8 | W(CO)$_6$ | MCPBA | 98.1 | 20.6 (21) | 77.5 (79) |
| 9 | W(CO)$_6$ | 50 wt % $H_2O_2/H_2O$ in CDCl$_3$ | 1.6 | — | 1.6 (100) |
| 10 | H$_4$O$_{40}$SiW$_{12}$·xH$_2$O | MCPBA | 0 | — | — |
| 11 | H$_4$O$_{40}$SiW$_{12}$·xH$_2$O | 50 wt % $H_2O_2/H_2O$ in CH$_3$OH | 13.7 | — | 13.7 (100) |
| 12 | V(acac)$_2$ | MCPBA | 0 | — | — |
| 13$^a$ | VO(acac)$_2$ | MCPBA | 9+ | — | 9 |

$^a$In addition to MCO, a number of by-products were formed which have not been characterized completely.
$^b$Percent selectivities for EMP or MCO based on reacted AMP are in parentheses.

No EMP was detected when MoO$_2$(acac)$_2$ was used as an epoxidation catalyst (Ex. 3 and 4), which suggests that any EMP formed cyclized to 8-methyl-3-chromanol. The conversion of AMP for the W(CO)$_6$-catalyzed reaction was far higher with MCPBA (Ex. 8) than with H$_2$O$_2$ (Ex. 9). EMP was observed with MCPBA as the oxidant in the W(CO)$_6$-catalyzed (Ex. 8) and MoO$_2$Cl$_2$-catalyzed (Ex. 5) reactions. The failure of AMP to react in Ex. 9 may be due to limited mass transfer between the two phases of the biphasic $H_2O_2$/$H_2O$+CDCl$_3$ reaction mixture. $H_2O_2$ was present in the aqueous phase, and the AMP was present in the organic phase (CDCl$_3$). Among all the catalysts tested, four catalysts were selected for their superior catalytic activity: MoO$_2$(acac)$_2$, MoO$_2$Cl$_2$, W(CO)$_6$, and H$_2$WO$_4$. Catalyst studies were conducted with sampling at regular time intervals to permit optimization of the reaction time, a parameter governing EMP yield.

Examples 15-18

Kinetic Studies of Metal-Catalyzed Epoxidation of 2-Allyl-6-Methylphenol

Amounts of AMP, EMP, and 8-methyl-3-chromanol as a function of reaction time for the metal-catalyzed epoxidations of AMP in Ex. 15-18 are plotted in FIGS. 5-8, respectively. In the figures, % conversion of AMP is represented by filled diamonds; EMT amount is represented by filled squares; and 8-methyl-3-chromanol amount is represented by filled triangles. For each example, the oxidant was MCPBA and the solvent was CDCl$_3$.

In Ex. 15 and FIG. 5, the conversion of AMP in the presence of MoO$_2$Cl$_2$ was about 60%. About 90% of this amount of AMP was consumed in the first 20 minutes. The amounts of EMP and 8-methyl-3-chromanol were both about 30%. By comparison, in Ex. 16 and FIG. 6, AMP conversion in the presence of the MoO$_2$(acac)$_2$ was only about 25%, and no EMP was observed beyond the first 20 minutes. Higher selectivity for EMP was observed with W-based catalysts compared to Mo-based catalysts. In Ex. 17 and FIG. 7, AMP conversion in the presence of tungstic acid was about 90%. The amounts of EMP and 8-methyl-3-chromanol were about 80% and about 10%, respectively. In Ex. 18 and FIG. 8, AMP conversion with W(CO)$_6$ was about 80%. About 80% of this amount of AMP was converted within the first 30 minutes. Amounts of EMP and 8-methyl-3-chromanol were about 70% and about 10%, respectively. As can be seen from FIG. 15-18, 8-methyl-3-chromanol was formed early in the reactions. Therefore optimization (minimization) of reaction time will not eliminate the formation of 8-methyl-3-chromanol.

Example 19

Thermoset Polymer Derived from 2-Allyl-6-Methyl Phenol

Efforts to directly confirm the formation of the EMP by $^1$H-NMR spectroscopy after first evaporating the methanol from the reaction product of Ex. 4 at about 60-70° C. under a blanket of nitrogen failed. Solvent removal resulted in the formation of a powder that was insoluble in both chloroform and DMSO, suggesting formation of a cross-linked polymer. Thermal analysis using DSC identified the insoluble powder to be a thermoset polymer having a glass transition temperature ($T_g$) of 241° C. Further thermal characterization of this material with TGA indicated char masses of 16.47%, 16.60% and 16.58% at 600, 700 and 800° C., respectively under air and char masses of 75.64% (600° C.), 70.81% (700° C.) and 62.90% (800° C.) when analyzed under a nitrogen atmosphere.

As used herein, the term "hydrocarbyl" and "hydrocarbon" refers broadly to a substituent comprising carbon and hydrogen, optionally with 1 to 3 heteroatoms, for example, oxygen, nitrogen, halogen, silicon, sulfur, or a combination thereof. The use of the terms "a", "an", "the", and similar referents in the context of describing the invention (especially in the context of the following claims) is to be construed to cover both the singular and the plural, unless otherwise indicated herein or clearly contradicted by context. "Or" means "and/or." The endpoints of all ranges directed to the same component or property are inclusive and independently combinable. Disclosure of a narrower range or more specific group in addition to a broader range or larger group is not a disclaimer of the broader range or larger group. All ranges disclosed herein are inclusive of the endpoints, and the endpoints are independently combinable with each other. The terms "first" and "second" and the like, as used herein do not denote any order, quantity, or importance, but are only used to distinguish one element from another. "Comprises" as used herein includes embodiments "consisting essentially of" or "consisting of" the listed elements.

Unless defined otherwise, technical and scientific terms used herein have the same meaning as is commonly understood by one of skill in the art to which this invention belongs. A "combination" is inclusive of blends, mixtures, reaction products, and the like.

While typical embodiments have been set forth for the purpose of illustration, the foregoing descriptions should not be deemed to be a limitation on the scope herein. Accordingly, various modifications, adaptations, and alternatives can occur to one skilled in the art without departing from the spirit and scope herein.

The invention claimed is:

1. A composition comprising 1 to 40 weight percent 2-(2,3-epoxypropyl)-6-methylphenol, 30 to 90 weight percent 2-allyl-6-methylphenol, and 1 to 40 weight percent 8-methyl-3-chromanol, based on the total weight of the 2-(2,3-epoxypropyl)-6-methylphenol, 2-allyl-6-methylphenol, and 8-methyl-3-chromanol.

2. A composition comprising 5 to 90 weight percent 2-(2,3-epoxypropyl)-6-methylphenol, 5 to 90 weight percent 2-allyl-6-methylphenol, and 1 to 20 weight percent 8-methyl-3-chromanol, based on the total weight of the 2-(2,3-epoxypropyl)-6-methylphenol, 2-allyl-6-methylphenol, and 8-methyl-3-chromanol.

* * * * *